United States Patent
Miller et al.

(10) Patent No.: US 12,342,887 B2
(45) Date of Patent: Jul. 1, 2025

(54) GARMENT (71) Applicant: It's Personal Girl, Inc., Chappaqua, NY (US)

(72) Inventors: Linda Miller, Chappaqua, NY (US); Suzanne Corra, Merrick, NY (US)

(73) Assignee: It's Personal Girl, Inc., Chappaqua, NY (US)

( * ) Notice: Subject to any disclaimer, the term of this patent is extended or adjusted under 35 U.S.C. 154(b) by 57 days.

(21) Appl. No.: 17/888,795

(22) Filed: Aug. 16, 2022

(65) Prior Publication Data

US 2023/0050850 A1 Feb. 16, 2023

Related U.S. Application Data (60) Provisional application No. 63/233,376, filed on Aug. 16, 2021.

(51) Int. Cl.
*A41D 31/12* (2019.01)
*A41B 9/00* (2006.01)
*A41D 1/06* (2006.01)

(52) U.S. Cl.
CPC ............ *A41D 31/125* (2019.02); *A41B 9/001* (2013.01); *A41D 1/06* (2013.01)

(58) Field of Classification Search
CPC ........... A41B 9/00; A41B 9/001; A41B 9/004; A41B 9/02; A41B 9/023; A41B 9/12; A41B 2400/22; A41B 2400/60; A41B 2400/62
USPC .............................. 2/400, 401, 402, 406, 272
See application file for complete search history.

(56) References Cited

U.S. PATENT DOCUMENTS

| | | | |
|---|---|---|---|
| 6,117,523 A * | 9/2000 | Sugahara | A61F 13/51121 428/137 |
| 10,441,479 B2 | 10/2019 | Griffiths | |
| 10,441,480 B2 | 10/2019 | Griffiths | |
| 2006/0264878 A1* | 11/2006 | Carstens | A61F 13/47227 604/402 |
| 2014/0018762 A1* | 1/2014 | Vignali | A61F 13/49006 604/385.14 |
| 2014/0039432 A1 | 2/2014 | Dubar et al. | |
| 2016/0113823 A1* | 4/2016 | Iwasaki | A61F 13/4704 604/385.26 |
| 2016/0302978 A1* | 10/2016 | Lindström | A61F 13/4704 |
| 2017/0290374 A1* | 10/2017 | Biodrowski | A41B 9/02 |
| 2017/0290714 A1* | 10/2017 | Norimoto | A61F 13/4752 |

(Continued)

*Primary Examiner* — Jameson D Collier
*Assistant Examiner* — Matthew R Marchewka
(74) *Attorney, Agent, or Firm* — Leason Ellis LLP (57) ABSTRACT

A garment is provided, the garment including a base fabric layer having an inner surface and an outer surface, the base fabric layer further having on the inner surface, an absorption region and a non-absorption region. In a particular implementation, the non-absorption region is configured to be in contact with the skin of a wearer of the garment. The garment further includes a moisture prevention insert that includes a moisture resistance layer in contact with the absorption region of the base fabric layer, wherein the moisture resistance layer includes at least two sub layers, each sub layer having a thermoplastic polyurethane coating; a fluid absorption layer configured in contact with the moisture resistance layer; and a mesh layer configured to have one surface thereof in contact with the fluid absorption layer and an opposing surface thereof in contact with the skin of the wearer.

13 Claims, 4 Drawing Sheets

(56) References Cited

U.S. PATENT DOCUMENTS

| | | | |
|---|---|---|---|
| 2019/0117476 A1* | 4/2019 | Bianchi | A61F 13/539 |
| 2020/0170309 A1* | 6/2020 | Ewell | B32B 27/12 |
| 2020/0214363 A1* | 7/2020 | Sakai | B29C 66/21 |
| 2020/0305515 A1 | 10/2020 | Bradley | |
| 2021/0162091 A1* | 6/2021 | Swamy | B29C 65/08 |
| 2021/0177676 A1* | 6/2021 | Kajanthan | A41B 9/12 |
| 2021/0368892 A1* | 12/2021 | Meng | A41D 31/12 |
| 2022/0040010 A1* | 2/2022 | Yoshiba | A61F 13/472 |

* cited by examiner

GARMENT

CROSS REFERENCE TO RELATED APPLICATION

The present application claims the benefit of priority to U.S. patent application Ser. No. 63/233,376, filed Aug. 16, 2021, which is hereby incorporated by reference in its entirety.

FIELD OF THE INVENTION

In various embodiments, the apparatus and methods described herein relate to garments configured to absorb or prevent the migration of bodily discharges through garments.

BACKGROUND

It is known and understood in the art to provide multi-function women's undergarments. For example, such undergarments are used to prevent the soiling of outer garments for women undergoing menstruation or incontinence. Typically, such undergarments are composed of multiple layers of bulk absorption material designed to prevent leaks or fluid discharges from migrating to the wearer's outer garments. However, while effective at fluid absorption, such designs and products are usually bulky. Such bulky configurations provide clothing profiles or outlines that render their use undesirable or uncomfortable. Additionally, products that incorporate bulk absorption materials can expose the wearer to prolonged exposure to fluid discharges. Such exposure can result in discomfort for the wearer or unsatisfactory sanitary conditions.

Attempts have been made to provide a suitable garment to address these concerns. For example, US20200305515A1 teaches sanitary underwear with a detachably attachable organic pad. Likewise, US2014039432A1 is directed to a multilayer leak-proof pad including a moisture-impermeable layer in contact with the fabric body: a moisture-absorbent layer thereover; and a moisture-wicking layer over the absorption layer. U.S. Pat. Nos. 10,441,479 and 10,441,480 also teach reusable sanitary underwear. While such approaches seek to describe a multifunction garment, these examples use insets, inserts or pads inserted into a wear's garment. Such inserts or add-on materials are not integrated into the garment in a manner to overcome the existing drawbacks in the art.

Thus, what is needed in the art is one or more apparatus, designs, or approaches that allow for a compact garment, such as an undergarment, that provides for effective fluid discharge absorption. Likewise, what is needed in the art is one or more apparatuses, designs or approaches that provide for a garment, such as an undergarment, that has additional stain prevention, moisture-wicking, antimicrobial management, and skin comfort functionality. Additionally, what is needed in the art is a garment with such properties that presents a low profile when worn by the wearer.

SUMMARY

In one particular implementation, a garment is provided. In a further implementation, the garment comprises a base fabric layer having an inner surface and an outer surface, the base fabric layer further having on the inner surface, an absorption region and a non-absorption region. In a particular implementation, the non-absorption region is configured to be in contact with the skin of a wearer of the garment. The garment further includes a moisture prevention insert. In one particular implementation, the moisture prevention insert is a multi-layer insert that includes a moisture resistance layer in contact with the absorption region of the base fabric layer, wherein the moisture resistance layer includes at least two sub layers, each sub layer having a thermoplastic polyurethane coating; a fluid absorption layer configured in contact with the moisture resistance layer; and a mesh layer configured to have one surface thereof in contact with the fluid absorption layer and an opposing surface thereof in contact with the skin of the wearer. In one particular implementation, a portion of the moisture resistance layer is bonded, stitched or through a combination thereof, adhered to a surface of the mesh layer not in contact with the fluid absorption layer.

In an alternative configuration, a method of manufacturing a garment is provided. For example, the method includes providing a multilayer moisture prevention insert to a base fabric layer, where the moisture prevention insert includes a moisture resistance layer in contact with the absorption region of the base fabric layer, wherein the moisture resistance layer includes at least two sub layers, each sub layer having a thermoplastic polyurethane coating. In a further implementation, the at least two sublayers have at least one urethane coating on each surface thereof. In a further configuration, the garment incudes a fluid absorption layer configured in contact with the moisture resistance layer; and a mesh layer configured to have one surface thereof in contact with the fluid absorption layer and an opposing surface thereof in contact with the skin of the wearer.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION OF CERTAIN EMBODIMENTS OF THE INVENTION

By way of example and broad overview, the apparatus described herein is a garment to be worn by a wearer. For ease of explanation, and simplicity of description only, the foregoing examples of such a garment are presented in the form of undergarments. However, it will be appreciated that that apparatus described herein can be fashioned into other styles of garments for other suitable purposes. For example, the garment can be presented in the form of pants, tights, one-piece units, swimwear, specialty utility apparel and the like. For example, the garment may include running shorts, bicycle shorts, swimwear, yoga pants, body-shape-altering "stretch" pants or shorts, sport or "performance" underwear, or any other such type or style of garment.

Figure 1:
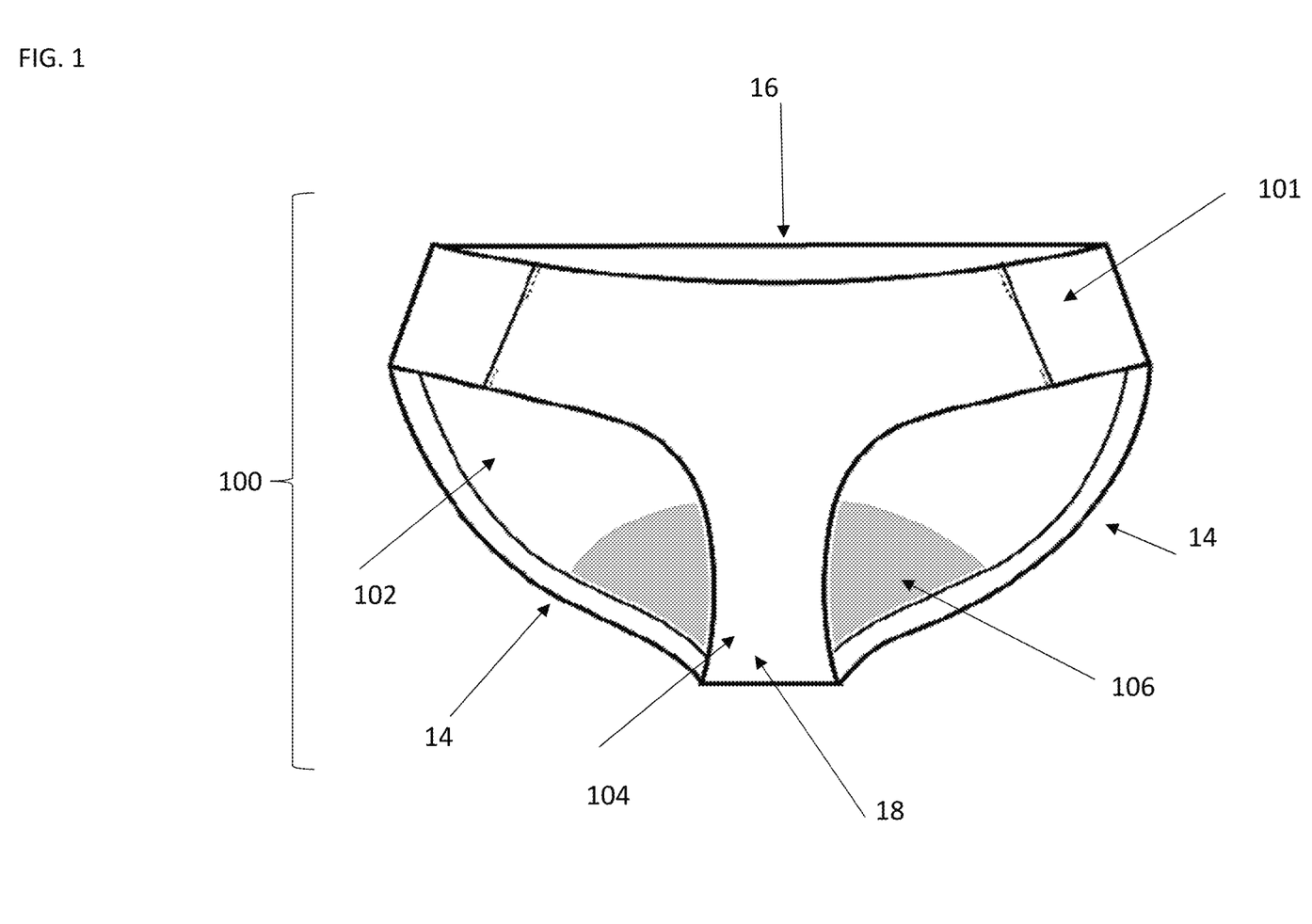
FIG. 1 depicts a garment in accordance with various embodiments of the invention.

Turning now to FIG. 1, an illustrative example of a garment 100 is provided. In one in the shown illustration, the garment 100 is configured as a "brief" style undergarment. As further shown, the brief style garment can include a waist opening 16 and a pair of leg openings 14 defining a crotch area 18. In the illustrated configuration, the garment includes a base garment layer 101.

In one or more implementations, the base garment layer 101 includes an interior surface 102. Here, the inner surface 102 of the base garment layer 101 is configured to be in contact with the body (such as but not limited to the skin) of the wearer. The base garment layer 101 of the garment 100 further includes an exterior surface 104. Here, the exterior surface faces away from the wearer when the garment is worn by the wearer. In one or more configurations, the inner surface 102 and the outer surface 104 are opposing sides of a single piece of fabric that forms the base garment layer 101. However, in alternative configurations, the base garment layer 101 is formed of multiple layers of fabric. In one implementation, base garment layer 101 includes two sub-layers. In such a configuration, a surface of one of the multiple layers of the base garment layer 101 is the exterior surface layer 104 and one surface of another of the multiple layers of the base garment layer is the interior surface 102 of the base garment layer 101.

It will be appreciated that the materials, shapes and designs of the one or more layers of the base garment layer 101 described herein are understood, appreciated and envisioned. For example, the one or more layers of the base garment layer 101 can have one or more colors, patterns, or designs. In one or more particular implementations, such as where the base garment layer 101 includes multiple layers, one or more of the multiple layers may not be visible to the wearer. Any number of layers or sub-layers of the base garment layer 101 is within the scope of the disclosure herein. Furthermore, the size, cut or other dimensions of the layers may be adjusted or adapted relative to one another so as to produce one or more different styles or designs of garment.

In one embodiment, the one or more layers of the base garment layer 101 are made of, or include, fabric formed of cotton, a cotton blend, a synthetic material, or any other material that is suitable for inclusion in a garment. For example, in one or more further implementations, a natural fiber, polyester or a polyester blend is used to from the base garment layer 101. In one or more implementations, one or more layers of the base garment layer 101 are formed of an elastic fabric or material. In yet a further implementation, one or more layers of the base garment layer 101 is formed an elasticized fabric blend such as spandex or a similar material that may provide support to the wearer and/or alter the shape of the body of the wearer. In one particular implementation, the base garment layer 101 is formed of a polyester or polyester blend fabric. In one particular implementation, the base garment layer 101 is 100% cotton. In one or more implementations, the cotton is recycled cotton. In another configuration, the base garment layer 101 is at least 50% cotton. In one or more further implementations, the base garment layer 101 is at least 80% cotton. In a further implementation, the base garment layer 101 is at least 90% cotton. In one particular implementation, the base garment layer 101 is between 50-95% cotton. In a further implementation, the base garment layer 101 is about 92% cotton. In a further arrangement, the base garment layer 101 includes both cotton and spandex or another polyether-polyurea copolymer. In one or more implementations, the base garment layer 101 further includes polyester. In one or more configurations, the base garment layer 101 includes spandex, polyester and cotton. In such a configuration, the base garment layer 101 includes about 92% cotton, about 8% polyester and spandex. In one or more further particular implementation, the base garment layer is formed out of 100% polyester or a polyester blend.

In a further arrangement, the base garment layer includes polyester, rayon and spandex. In one or more implementations the base garment layer has a grams per square meter (GSM) of between 50 and 200 gsm. In a particular implementation, the base garment layer 101 has a gsm of about 149. However, it should be appreciated that any GSM value for a fabric or material is contemplated and understood.

In yet a further configuration, the base garment layer 101 is coated with a water or liquid repellent coating. In yet a further implementation, the base garment 101, or one or more sub-layers thereof, is constructed from a durable water repellant material. For example, where the base garment layer 101 is composed of one or more sub-layers, at least one of the sub-layers is constructed from a material that have been coated with a liquid repellant substance or compound.

In one or more particular implementations multiple layers of the base garment fabric are joined together by stitching, adhesives, thermal bonding or other techniques known or understood in the art. For example, the seams or portions of the garment are joined or bonded through the use of seam tape. In an alternative configuration, the seams or portions of the garment are joined through the use of stitching. In a further example, the seams or portions of the garment are joined or bonded through a combination of seam tape and stitching.

Continuing with the illustrated implementation in FIG. 1, a multi-layer insert 106 is also provided in the garment 100. In one or more implementations, the multi-layer insert 106 is attached to the inner surface 102 of the base layer garment 101. For example, the multi-layer insert 106 is attached by stitching, gluing, thermal bonding or other methods known and understood in the art. In one or more further implementations, the multilayer insert 106 is attached to the base garment layer 101 by seam tape.

As provided in the illustrated configuration, in one arrangement, the multi-layer insert may be disposed in a crotch area 18 of the garment 100, when the garment 100 is configured as an undergarment. However, it will be appreciated that the multi-layer insert 106 could be positioned at other locations relative to the wearer in alternative configuration or arrangements. In one or more implementations, the multi-layer insert 106 is configured to extend over some or all of the crotch area and/or extend beyond the crotch area of a garment 100 configured as an undergarment. In one or more embodiments, the multi-layer insert 106 can be configured in any cut, size, style, color or type suitable for inclusion in the garment.

Figure 2:
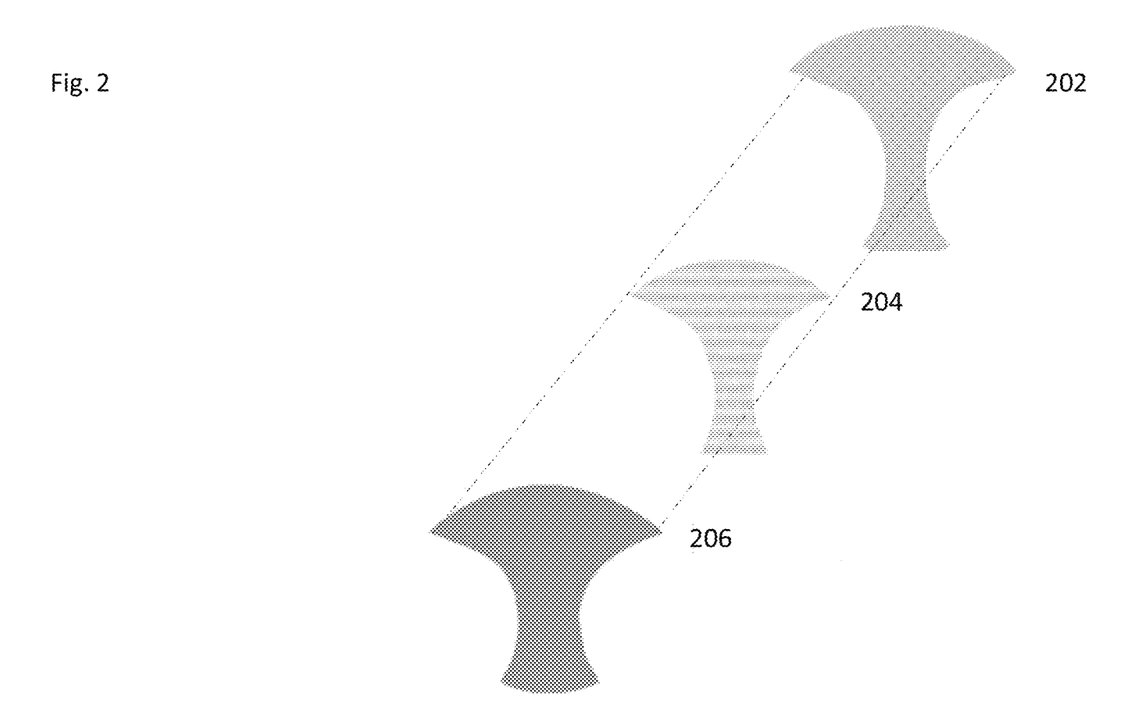
FIG. 2 depicts an exploded view of a multi-layer insert of the garment in accordance with an embodiment of the invention.

Turning now to the illustration of FIG. 2, the multi-layer insert 106 can include at least three (3) layers of fabric or material. In one or more configurations, the multi-layer insert 106 is configured to absorb liquid, including but not limited to bodily secretions, menstrual fluids or other fluid discharges of the wearer. In one or more further implementations, the multi-layer insert 106 is configured to prevent or reduce leakage of fluid discharges.

In one configuration, the multi-layer insert 106 includes at least one breathable mesh lining layer 202 that is configured to be in close proximity to the wearer of the garment 101. In the same or another configuration, the multi-layer insert 106 includes a fluid absorption layer 204 configured to be in contact with the mesh lining layer 202. In the same or yet a further configuration, the multi-layer insert 106 also includes a multi-layer moisture impermeable layer 206 that is configured to prevent fluid discharges from migrating away from the multi-layer insert 106. In one or more implementations, each layer is bonded to the next layer. For example, the mesh lining layer 202, fluid absorption layer 204 and moisture impermeable layer 206 are bonded to one another using seam tape or another bonding process. In an alternative configuration, the seams or portions of the garment are joined through the use of stitching. In a further example, the seams or portions of the garment are joined or bonded through a combination of seam tape and stitching.

In one particular implementation, the mesh lining layer 202 is a single mesh fabric with anti-bacterial and/or stain resistant finishes. For instance, and in no way limiting, the mesh lining layer 202 is impregnated or coated with one or more micro- or nanoparticles that have anti-microbial properties. For example, the mesh lining layer 202 is coated in particles such as silver, zinc or copper and/or oxides thereof. In one particular implementation, the mesh lining layer 202 is formed of a polyester or polyester blend fabric. In one particular implementation, the mesh lining layer is 100% polyester. In another configuration, the mesh lining layer 202 is at least 50% polyester. In one or more further implementations, the mesh lining layer 202 is at least 80% polyester. In a further implementation, the mesh lining layer 202 is at least 90% polyester. In one particular implementation, the mesh lining layer 202 is between 50-95% polyester. In a further implementation, the mesh lining layer 202 is about 94% polyester. In a further arrangement, the mesh lining layer includes both polyester and spandex. In one or more implementations, the amount of polyester to spandex in the mesh lining layer 202 is 94% polyester and 6% spandex. In one or more implementations, the amount of polyester spandex in the moisture-absorbent layer 204 is 92% polyester and 8% spandex. In one or more implementations the mesh lining layer 202 has a grams per square meter (GSM) of between 50 and 280 gsm. In a particular implementation, the mesh lining layer 202 has a gsm of about 100-124. In a particular implementation, the mesh lining layer 202 has a gsm of about 115. However, in one or more further configurations, the GSM of the mesh lining layer is selected based on desired properties of the garment layer.

In one or more further implementations, one or more of the fabrics comprising the mesh lining layer 202 are treated with one or more hydrophilic or hydrophobic compositions or materials. For example, the mesh lining layer 202 is treated in one configuration with polyethylene oxide, polyvinyl alcohol, polyacrylamide, poly acrylic acid, polyvinyl pyrrolidone, hydrophilic silicones, or hydrophilic polyurethanes) and/or a hydrophobic composition or material. In one or more further implementations, the mesh lining layer 202 includes one or more silicones, polyfluoroalkylacrylates, polyacrylates, polyurethanes, or waxes) or other material used to create a hydrophilic or hydrophobic surface.

Returning to FIG. 2, as shown, the multilayer insert 106 includes a moisture-absorbent layer 204 that is positioned to abut or be in direct contact with the mesh lining layer 202. For example, the moisture-absorbent layer 204 is configured to be bonded, stitched (or a combination thereof) or otherwise joined to a surface of the mesh lining layer that is opposite the surface presented to the wearer of the garment 101. In one or more configurations, the moisture absorbent layer 204 is configured to absorb liquid discharges that have passed though the mesh layer 202. In one particular implementation, the moisture-absorbent layer 204 is a single piece fabric with anti-bacterial and/or stain resistant finishes. For instance, and in no way limiting, the moisture-absorbent layer 204 is impregnated or coated with one or more micro or nanoparticles that have anti-microbial materials. For example, the moisture-absorbent layer 204 is coated with materials such as zinc or copper oxides.

The inventors of the described subject matter have determined specific configurations of the mesh lining layer 202 and the moisture-absorbent layer 204 can result improved performance relative to the art. For example, it has been discovered by the inventors that where the mesh lining layer 202 includes one or more hydrophobic coatings, the moisture-absorbent layer 204 is less capable of absorbing the discharged liquid. Without being held to any particular theory, the hydrophobic coating of the mesh lining layer 202 interferes with the hydrophilic materials provided as part of the moisture-absorbent layer 204. Thus, in one particular configuration, the moisture-absorbent layer 204 is configured to abut or be bonded, stitched or otherwise adhered to a mesh lining layer 202 that lacks a hydrophobic coating.

In one particular implementation, the moisture-absorbent layer 204 is formed of a polyester or polyester blend fabric. In one particular implementation, the moisture-absorbent layer 204 is 100% polyester. In one or more implementations, the polyester is recycled polyester. In another configuration, the moisture-absorbent layer 204 is at least 50% polyester. In one or more further implementations, the moisture-absorbent layer 204 is at least 80% polyester. In a further implementation, the moisture-absorbent layer 204 is at least 90% polyester. In one particular implementation, the moisture-absorbent layer 204 is between 50-95% polyester. In a further implementation, the moisture-absorbent layer 204 is about 94% polyester. In a further arrangement, the moisture-absorbent layer 204 includes both polyester and spandex. In one or more implementations, the amount of polyester to spandex in the moisture-absorbent layer 204 is 94% polyester and 6% spandex. In one or more implementations, the amount of polyester to spandex in the moisture-absorbent layer 204 is 92% polyester and 8% spandex. In a further arrangement, the moisture-absorbent layer 204 includes polyester, rayon and spandex. In one or more implementations, the amount of polyester relative to the amount of rayon and spandex in the moisture-absorbent layer 204 is 66% polyester, 31% Rayon and 3% spandex.

In one or more implementations the moisture-absorbent layer 204 has a grams per square meter (GSM) of between 50 and 280 gsm. In a particular implementation, the moisture-absorbent layer 204 has a gsm of about 200-215. In a particular implementation, the moisture-absorbent layer 204 has a gsm of about 210. However, it should be appreciated that any GSM value for a fabric or material is contemplated and understood. In one or more configurations, the moisture absorbent layer 204 is configured that upon absorption of discharged fluid, the dimensions of the moisture absorbent layer 204 do not increase by more than 3%, 5% or 10% relative to the original dimensions (width, length, thickness) of the moisture absorbent layer 204 when it has not absorbed any fluid.

The moisture-absorbent layer 204 includes, in one or more implementations, a first surface and a second surface. In one particular implementation, the first surface is configured to abut or be in contact with the mesh layer 202. In a further example, the first surface of the moisture-absorbent layer 204 is configured to include pique texturing or knit fabric. For instance, the moisture-absorbent layer 204 includes one or more raised parallel cords of fabric or material. The second surface of the moisture-absorbent layer 204 is configured to lack such a pique or textured surface and is configured to bind or abut the moisture impermeable layer 206. It will be appreciated that such a pique or textured surface abutting the mesh layer will improve the migration of moisture away from the mesh layer 202 and into the moisture-absorbent layer 204.

Continuing with FIG. 2, the moisture-impermeable layer 206 may comprise, consist of, or include any wholly or partially moisture-blocking material known in the art. In one or more implementations, the moisture impermeable layer 206 is composed of one or more layers of fabric or material. In one particular implementation, the moisture-impermeable layer 206 is composed of two sub-layers of fabric. Each of these fabric layers includes a base fabric and a thermoplastic polyurethane (TPU) coating or layer. In one or more implementations, two layers of moisture-impermeable fabric are combined so that the respective TPU coatings are paired. For instance, the TPU coating of a first one of the moisture-impermeable layer 206 is configured to bond with, or be adhered to, the TPU layer of the second moisture-impermeable layer 206.

Figure 4:
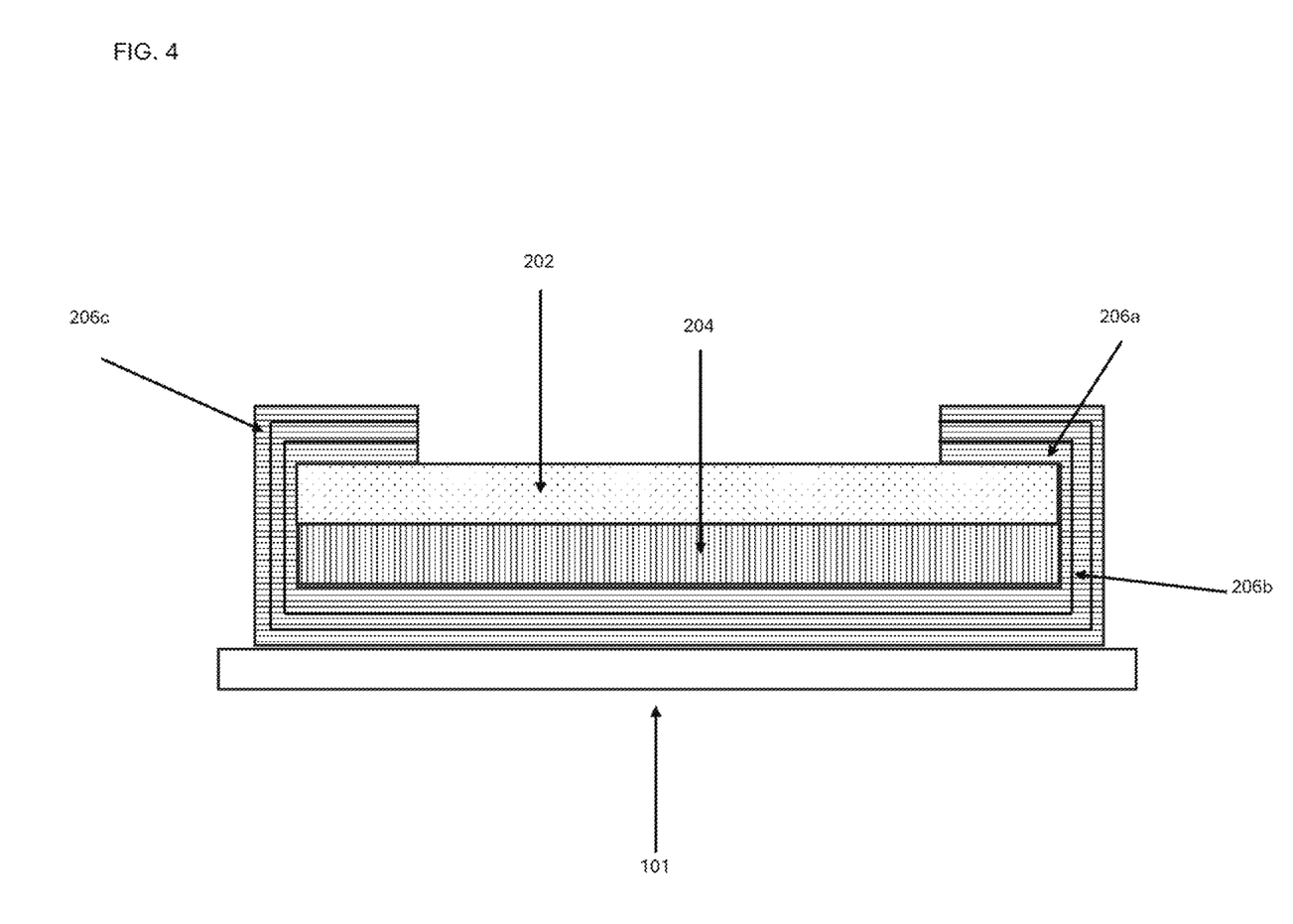
FIG. 4 depicts aside cross-sectional view of the garment and multi-layer insert in accordance with an embodiment of the invention.

The inventors have found that thermally bonding the TPU material of a moisture-impermeable layer 206 to a moisture absorption layer 204 results in decreased performance relative to expectations. In the art, multiple layers of fabric are typically bonded to one another using a thermal adhesion process. Without being held to any particular theory, when a TPU material is thermally bonded to an absorption layer, the impermeable characteristics are degraded. The TPU layers melt, resulting in an inconsistent interface between that the moisture-impermeable layer 206 and the moisture-absorbing layer 204. This inconsistency in the interface between the two layers causes liquid to migrate to the rest of the garment. The described configuration overcomes this drawback by orientating the TPU coating or layer of the moisture-impermeable layer 206 away from the surface thereof that is configured to be in contact with the absorption layer. Additionally, the moisture-impermeable layer 206 is bonded using adhesives. In this configuration, the TPU layers of the sub-layers of the moisture-impermeable layer 206, when thermally bonded do not melt and form an inconsistent interface with the moisture-absorption layer 204. Thus, the described approach allows for an improved overall garment, and in particular, an improved interface between the moisture-impermeable layer 206 and the moisture absorption layer 204. In one or more further implementations, the moisture-impermeable layer 206 includes a second TPU layer or coating on an alternate surface of the fabric. As shown in FIG. 4, the moisture-impermeable layer 206 has a first TPU layer 206a, an inner fabric core 206b and a second TPU layer or coating 206c. In one or more implementations, the moisture-impermeable layer 206 is configured to create a leak-proof barrier against leakage of the liquid flow from the moisture-absorbent layer 204.

Figure 3:
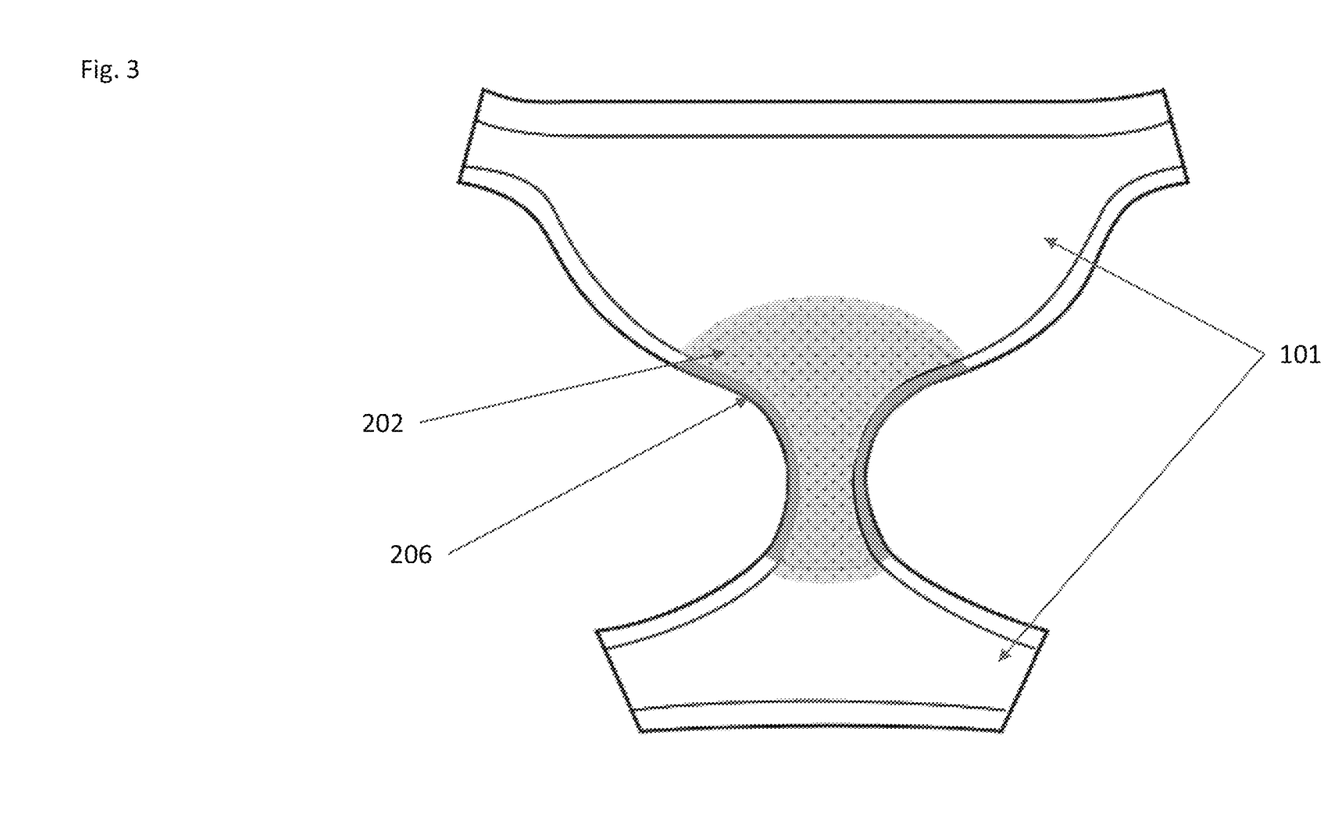
FIG. 3 depicts a structure of a multi-layer insert attached to the garment in accordance with an embodiment of the invention.

In yet a further implementation, the moisture-impermeable layer 206 is configured so as to encompass at least a portion of the moisture-absorbent layer 204 and the mesh lining layer 202. For example, as shown in FIGS. 3 and 4, the moisture-impermeable layer 206 is sized to envelop the sides of the moisture-absorbent layer 204 and a portion of the mesh lining layer 202. In this configuration, liquid that has migrated from the mesh lining layer 202 to the moisture absorbent layer 204 is prevented from leaking or further migrating to the wearer's skin or to the base garment layer 101.

As shown in more detail in FIG. 4, the garment is composed on at least four (4) layers. As shown, the mesh lining layer 202 is joined, on one surface, to the moisture-absorbent layer 204. In the provided illustration, the moisture-impermeable layer 206 is configured to enclose a portion of the mesh lining layer 202. For example, a portion of the moisture-impermeable layer 206 is configured to envelop the edges of the mesh lining layer 202. In the provided illustration, the moisture-absorbent layer 204 is surrounded on three (3) surfaces by the moisture-impermeable layer 206 and on one surface by the mesh lining layer 202. In this configuration, the moisture-impermeable layer 206 prevents fluid from migrating away from the moisture-absorbent layer 204 while still allowing the migration of moisture to the moisture-absorbent layer 204 via the mesh lining layer 202.

As shown in FIG. 3, in a further implementation, the moisture-impermeable layer 206 is configured to envelop at least five (5) sides or surfaces of the mesh lining layer 202 and moisture-absorbent layer 204. Here, the only portion of the mesh lining layer 202 that is not enveloped by the moisture-impermeable layer 206 is that side that is to be in direct contact with the wearer. However, in further configurations, at least a portion of the surface of the mesh lining layer 202 to be in contact with the wearer is enclosed by the moisture-impermeable layer 206, as shown in FIG. 4.

In one particular implementation, the fabric portion of the moisture-impermeable layer 206 may be made of conventional knitted fabric materials, such as a blend of nylon lycra (a type of spandex fiber), spandex, silk, cotton, etc., and therefore may be manufactured using conventional stitching approaches for fabrics. In one particular implementation, the moisture-impermeable layer 206 is formed of a polyester or polyester blend fabric. In one particular implementation, the moisture-impermeable layer 206 is 100% polyester. In one or more implementations, the polyester is recycled polyester. By way of non-limiting example, the recycled material can be recycled from water bottles or other beverage containers. In a further particular example, the recycled material is dyed so as to ensure that the color of the recycled material matches the colors provided or provided in non-recycled materials.

In another configuration, the moisture-impermeable layer 206 is at least 50% polyester. In one or more further implementations, the moisture-impermeable layer 206 is at least 80% polyester. In a further implementation, the moisture-impermeable layer 206 is at least 90% polyester. In one particular implementation, the moisture-impermeable layer 206 is between 50-95% polyester. In a further implementation, the moisture-impermeable layer 206 is about 94% polyester. In a further arrangement, the moisture-impermeable layer 206 includes both polyester and spandex. For example, the fabrics described herein can include about 92% polyester, and about 8% spandex or another similar material. In a further arrangement, the moisture-impermeable layer 206 includes polyester, rayon and spandex in an amount greater than 10%.

In one or more implementations the moisture-impermeable layer 206 has a grams per square meter (GSM) of between 50 and 280 gsm. In a particular implementation, the moisture-impermeable layer 206 has a gsm of about 56. However, it should be appreciated that any GSM value for a fabric or material is contemplated and understood.

The garment described herein includes various advantages over prior approaches and solutions in the art. For example, the garment described herein has improved leak prevention, stain prevention, moisture-wicking comfort, antimicrobial management and liquid absorption compared to existing solutions. Furthermore, the present garment provides the wearer with an effective and discrete solution to manage unwanted fluid discharge events while maintaining a low garment profile. It will be appreciated that the fluid absorption layer 204 operates to prevent the migration of fluid to the outer base layer(s) by absorbing or otherwise sequestering the liquid. Furthermore, the moisture impermeable layer further operates to constrain the migration of the liquid by providing one or more TPU layers that prevent the passage of liquid. These features, when combined, provide for a low profile, moisture retaining, garment that can be adapted for multiple uses and configurations.

The garment disclosed herein should not be limited or constrained to the four layers as described above. For example, as described herein, additional other layers may be incorporated in between or outside the five-layer structure for providing additional absorption support, decoration, or any other functionality. In addition, the ordering of the layers in the above-described five-layer structure may be interchanged to the extent that the key functionalities, including moisture wicking, leak and stain resistance, and antimicrobial support, are retained and further supported by such an ordering.

Additionally, in various alternative embodiments the fibrous materials described in specific embodiments herein may be substituted by materials that would be recognizable as compatible by those skilled in the art. Further, the chemicals, compounds, stains, dyes and other treatments or elements of the garment, its design, or the process by which it is created may be substituted with other known materials recognized by those skilled in art, including but not limited to hydrophilic elements, hydrophobic elements, sealants, foams, and others. The various components or subparts of an embodiment may be substituted and used with other subparts of other embodiments and various combinations thereof, provided the claimed functionalities or general purpose of the design is preserved.

In an alternative configuration, a method of manufacturing a garment is provided. For example, the method includes providing a multilayer moisture prevention insert to a base fabric layer, where the moisture prevention insert includes a moisture resistance layer in contact with the absorption region of the base fabric layer, wherein the moisture resistance layer includes at least two sub layers, each sub layer having a thermoplastic polyurethane coating. In a further implementation, the at least two sublayers have at least one urethane coating on each surface thereof. In a further configuration, the garment incudes a fluid absorption layer configured in contact with the moisture resistance layer; and a mesh layer configured to have one surface thereof in contact with the fluid absorption layer and an opposing surface thereof in contact with the skin of the wearer.

While this specification contains many specific embodiment details, these should not be construed as limitations on the scope of any embodiment or of what can be claimed, but rather as descriptions of features that can be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, the phraseology and terminology used herein is for the purpose of description and should not be regarded as limiting. The use of "including." "comprising," or "having." "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

Publications and references to known registered marks representing various systems are cited throughout this application, the disclosures of which are incorporated herein by reference. Citation of any above publications or documents is not intended as an admission that any of the foregoing is pertinent prior art, nor does it constitute any admission as to the contents or date of these publications or documents. All references cited herein are incorporated by reference to the same extent as if each individual publication and references were specifically and individually indicated to be incorporated by reference.

While the invention has been particularly shown and described with reference to preferred embodiments thereof, it will be understood by those skilled in the art that various changes in form and details may be made therein without departing from the spirit and scope of the invention. As such, the invention is not defined by the discussion that appears above, but rather is defined by the claims that follow, the respective features recited in those points, and by equivalents of such features.

What is claimed is:

1. A garment comprising:
  a base fabric layer having an inner surface and an outer surface, wherein the base fabric layer further having on the inner surface, an absorption region and a non-absorption region, wherein the non-absorption region is configured to be in contact with a skin of a wearer of the garment; and a moisture prevention insert comprising a moisture resistance layer in contact with the absorption region of the base fabric layer, wherein the moisture resistance layer includes at least two sub-layers, each sub-layer further comprising a first thermoplastic polyurethane layer adhered to a first surface of a core fabric layer and a second thermoplastic polyurethane layer adhered to a second surface of the core fabric layer; a fluid absorption layer formed of an absorbent fabric and having a first surface with a plurality raised fabric cords, and an opposing second surface lacking a plurality of raised fabric cords, wherein the second surface is adhered to the first thermoplastic polyurethane layer of one of the sub-layers of the moisture resistance layer; and a mesh layer having a first surface and a second surface, the first surface of the mesh layer being in contact with the first surface of the fluid absorption layer and the second surface of the mesh layer being configured to be at least partially in contact with the skin of the wearer, wherein a portion of the moisture resistance layer is joined to the first surface of the mesh layer.

2. The garment of claim 1 wherein the mesh layer comprises a single mesh fabric with one or more antimicrobial or stain-resistant coatings.

3. The garment of claim 1 wherein the garment is configured as an undergarment.

4. The garment of claim 3 wherein the thermoplastic polyurethane layer of at least one of the at least two sub-layers is bonded to a thermoplastic polyurethane layer of a second of the at least two sub layers.

5. The garment of claim 3 wherein at least one of the at least two sub-layers of the moisture resistance layer extends as a unitary panel beyond the fluid absorption layer to bond with the second surface of the mesh layer.

6. The garment of claim 1, wherein the base fabric layer is comprised of at least 90% cotton.

7. The garment of claim 1, wherein the base fabric layer is comprised of at least 90% blended polyester.

8. The garment of claim 7, wherein the base fabric layer is comprised of at least 8% spandex.

9. The garment of claim 1 wherein the fluid absorption layer comprises at least 51% cotton.

10. The garment of claim 1, wherein the fluid absorption layer is comprised of polyester.

11. The garment of claim 1, wherein the fluid absorption layer is comprised of about 66% rayon, about 31% polyester and about 3% spandex.

12. The undergarment of claim 1 wherein the fluid-absorbent layer comprises cotton.

13. The undergarment of claim 1 wherein the fluid-absorbent layer comprises foam.

* * * * *